US005759772A

United States Patent [19]
Kirkpatrick et al.

[11] Patent Number: 5,759,772
[45] Date of Patent: Jun. 2, 1998

[54] METHOD FOR DETERMINING THE SEX OF AN EMBRYO

[75] Inventors: Brian W. Kirkpatrick; Ricky L. Monson, both of Madison, Wis.

[73] Assignee: Wisconsin Alumni Research Foundation, Madison, Wis.

[21] Appl. No.: 255,105

[22] Filed: Jun. 7, 1994

Related U.S. Application Data

[63] Continuation of Ser. No. 919,536, Jul. 23, 1992, abandoned.
[51] Int. Cl.[6] ............................................. C12Q 1/68
[52] U.S. Cl. .................. 435/6; 435/91.2; 536/24.31; 536/24.33
[58] Field of Search .................. 435/6, 91.2; 536/24.31, 536/24.33

[56] References Cited

PUBLICATIONS

Sambrook et al., "Molecular Cloning," Pub. by Cold Spring Harbor Laboratory Press (1989) pp. 11.45–11.47.
Sommer, Nucleic Acids Res. vol. 17, No. 16 p. 6749. (1989).
Gyllensten in "PCR Technology," ed. by Henry A. Erlich, Stockton Press: New York. Chapter 5, pp. 45–60. (1989).
Arnheim in "PCR Technology," ed. by Henry A. Erlich, Stockton Press: New York. Chapter 12 pp. 119–135. (1989).
Herr, et al., "Rapid, Accurate Sexing of Livestock Embryos," Proceedings of the Fourth World Congress on Genetics Applied to Livestock Production, W. G. Hill, et al., Eds. vol. XVI:334–343 (1990).
Aasen, et al., "Amplification of the ZFY and ZFX Genes for Sex Identification in Humans, Cattle, Sheep and Goats," Biotechnology 8:1279–1281 (1990).

Peura, et al., "A Reliable Sex Determination Assay for Bovine Preimplantation Embryos Using the Polymerase Chain Reaction," Theriogenology 35:547–555 (1991).
Handyside, et al., "Pregnancies from biopsied human pre-implantation embryos sexed by Y-specific DNA amplification," Nature 344:768–770 (1990).
Schultz, G. A., Polymerase Chain Reaction (PCR) Applications in Reproductive Biology, Medical Biochemistry pp. 1–6, University of Calgary Press, Calgary, Alberta, Canada (1991).
Curran, Sandra, "Fetal Sex Determination in Cattle and Horses by Ultrasonography," Theriogenology 37:17–21 (1992).
Wachtel, S. "H–Y Antigen in the Study of Sex Determination and Control of Sex Ratio," Theriogenology 21:18–27 (1984).
Wachtel, et al., "Sex Selection with Monoclonal H–Y Antibody," Fertility and Sterility 50:355–360 (1988).

Primary Examiner—Scott W. Houtteman
Attorney, Agent, or Firm—Quarles & Brady

[57] ABSTRACT

A method for determining the sex of a mammalian embryo is disclosed. This method begins with the isolation of an embryonic cell that contains pseudo-autosomal DNA sequences. At least a portion of the pseudo-autosomal DNA sequences are amplified, creating pseudo-autosomal DNA fragments. Allele-specific DNA sequences are amplified using the pseudo-autosomal DNA fragments as a template and allele-specific primers. The allele-specific products are examined for the presence or absence of the X-allele-specific and Y-allele-specific products. Preferably, the embryo is bovine and the pseudo-autosomal DNA sequences are ZFX and ZFY. Also preferably the allele-specific primers are those described in Sequence ID NOS: 5, 6, 7 and 8.

13 Claims, 4 Drawing Sheets

FIG. 1

```
-ACCAGCAAG  GCGGAGAAGGC  CATTGAATGC  GATGAGTGCG  GAAAGCATT
T.........  T.A........  ...C.....T  .....C..T.  .G.......
            ─────────────────────────────────────▶ 5'Y

TCTCTCATGC  TGGGGCTTTG   TTTACTCATA  AAATGGTGCA  TAAGGAAAAA
....C.....  ..........   ..C.....C.  ..........  ..........

GGAGCTAACA  AAATGCACAA   ATGTAAATTC  TGTGAATACG  AGACAGCTGA
.....C.G..  .......T..   ..........  .....G..T.  ──────────

ACAAGGGTTA  CTGAATCGCC   ACCTTTTGGC  GGTCCATAGC  AAGTACTTTC
..........  T.A.......   ..........  A.....C...  ...A......
─────────────▶ 5'X
   3'Y ◀────────────────────────────

CTCATATATG  CGTGGAGTGT   GGTAAAGGTT  TTCGTCATCC  ATCAGAGCTC
.C........  T..A......   ..........  ......C..  ..........

AAAAAGCACA  TGCGAATCCA   TACTGGCGAG  AAGCCGTACC  AGTGCCAGTA
..........  ..........   ......A...  ..A.......  .A........

CTGCGAATAT  AGGTCCGCAG   ACTCTTCTAA  CTTGAAAACG  CATGTAAAAA
..........  ....T.....   ..........  T.....G...  .....G....

CTAAGCATAG  TAAAGAGATG   CCATTCAAGT  GTGACATTTG  TCTTCTG
..........  ......A...   T.T.......  ..........  .......
                   3'X ◀────────────────────────
```

UPPER SEQUENCE IS ZFX. CORRESPONDING BASES WHICH ARE IDENTICAL IN ZFY ARE DENOTED BY DOTS, OTHERWISE THE SUBSTITUTED BASES ARE DENOTED.

METHOD FOR DETERMINING THE SEX OF AN EMBRYO

This is a continuation of application Ser. No. 07/919,536 filed Jul. 23, 1992 now abandoned.

STATEMENT REGARDING FEDERALLY SPONSORED RESEARCH

This invention was made with United States government support awarded by the United States Department of Agriculture (USDA) Hatch Funds. The United States Government has certain rights in this invention.

FIELD OF THE INVENTION

The field of the present invention is sex-determination assays. Specifically, the field of the present invention is sex determination assays of mammalian embryo cells that involve amplification of pseudo-autosomal regions of the X and Y chromosomes.

BACKGROUND

The ability to determine animal gender could improve efficiency of animal production and animal selection. In beef production, the ability to produce only female offspring would facilitate use of a single-calf heifer system. In a perfect beef production system, each dam would produce one female calf which would serve as its replacement. Beef production efficiency would be improved through reduction of cow maintenance costs. In dairy systems, sex determination would permit the specific production of either male or female embryos. In commercial dairy operations, female embryos of high genetic merit would be preferred for use as replacement stock. Artificial insemination organizations making planned matings would prefer males for their potential value as sires.

A reliable method of sex determination is required for such a system. Several methods have now been reported for mammalian sex determination. Handyside, et al. (*Nature*, 344:768-770, 1990) used polymerase chain reaction (PCR) to amplify a Y-chromosome-specific repeat sequence, DYZI, that is present 500-8000 times on the Y chromosome. The presence of this amplified target sequence indicates the presence of the Y-specific DNA sequence in the sample DNA and, hence, indicates that the animal is male. A disadvantage of the Handyside et al. technique is that the absence of the amplified target sequence may be due either to the absence of the sequence in the sample DNA or to a failed reaction.

Another method involves PCR-based genotyping, Aasen and Medrano, *Bio/Technology* 8:1279-1281 (1990); Herr et al., *Proceedings of the 4th World Congress on Genetics Applied to Livestock Production*, W. G. Hill et al., eds. Vol XVI:334-343, (1990). In brief, a pseudo-autosomal region (common to both X and Y chromosomes) present in both X and Y chromosomes is amplified. These homologous regions are called ZFY (in the Y chromosome) and ZFX (in the X chromosome). The amplified product is then digested with restriction enzymes that take advantage of restriction enzyme fragment length polymorphisms between ZFY and ZFX. The digested DNA is separated via electrophoresis. The ZFX and the ZFY DNA are identified by their different digestion patterns.

Another PCR-mediated approach uses three sets of primers for sex determination of pre-implantation bovine embryos. (Peura, et al., *Theriogenology*, 35[3]:547-555,

2

1991). As a positive control, the first set of primers amplifies a bovine-specific satellite DNA sequence. Thus, both male and female samples have this amplified target sequence. Two pairs of primers that recognize repetitive bovine Y-chromosome-specific sequences are then used in a PCR amplification reaction.

Another approach to sexing embryos involves the detection of sex-specific antigen (Watchel et al., *Theriogenology* 21:18-27, 1984).

What is needed in the art is an improved method of sex determination which would offer greater sensitivity, an improved positive control, less likelihood of sex misclassification from non-bovine DNA contamination and faster results.

SUMMARY OF THE INVENTION

The present invention is a method for determining the sex of a mammalian embryo. This method begins with the isolation of DNA containing pseudo-autosomal sequences from an embryonic cell. These pseudo-autosomal DNA sequences are then amplified to create pseudo-autosomal DNA fragments. The pseudo-autosomal DNA fragments are used as templates to amplify X-allele-specific and Y-allele-specific DNA fragments, with the help of allele-specific primers. The DNA created is examined for the presence or absence of allele-specific products.

Preferably, the amplification is by PCR, and the pseudo-autosomal regions are the ZFX and ZFY regions. Also preferably the X-allele-specific and Y-allele-specific primers are sequence ID NOS: 5, 6, 7 and 8. Also preferably, the embryo is bovine.

It is an object of the present invention to determine the sex of a mammalian embryo.

It is another object of the present invention to determine the sex of a bovine embryo.

An advantage of the present invention is that allele-specific products are produced.

It is another advantage of this present invention that these allele-specific products are of different size.

It is another advantage of the present invention that the allele-specific products are in equal molar amounts.

It is another advantage of the present invention that at least one of the allele-specific primers is species specific.

It is another advantage of the present invention that the amplified DNA does not have to be digested with restriction enzymes.

Other objects, advantages and features of the present invention will become apparent after examination of the specification, claims and drawings.

BRIEF DESCRIPTION OF THE DRAWINGS

FIG. 3 is a set of stained gels produced by the method of the present invention. The gel of FIG. 3(a) contains 12 bovine female DNA samples. The gel of FIG. 3(b) contains 12 bovine male DNA samples.

BRIEF DESCRIPTION OF THE INVENTION

1. In General

Figure 1:
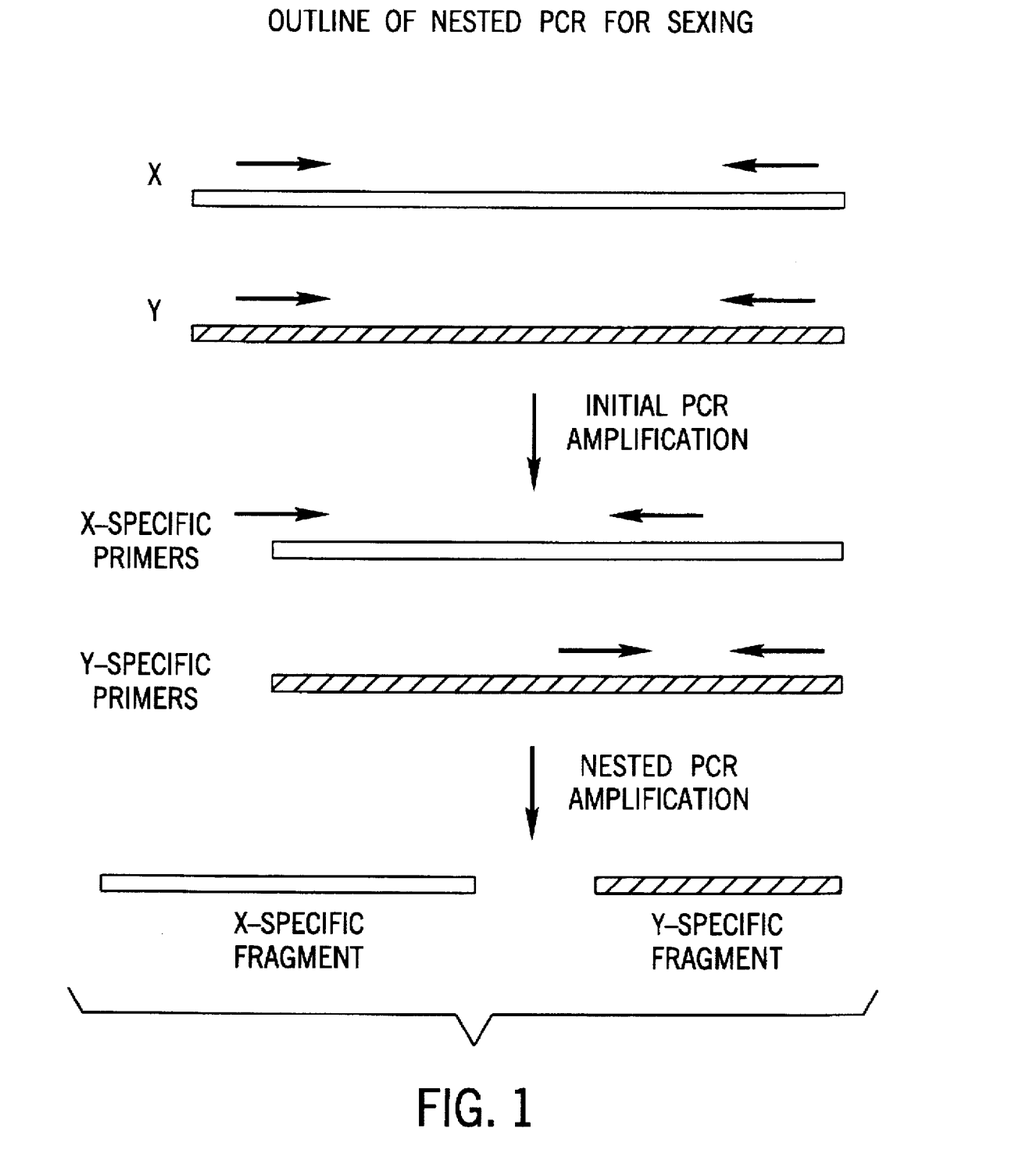
FIG. 1 is a flow chart of an embodiment of the present invention.

The present invention is a rapid method of sex determination of embryos with improved sensitivity and controls relative to previous methods. FIG. 1 is a flow chart of one embodiment of the present invention. In general, the method is based on a cloned and sequenced approximately 400 bp segment of the pseudo-autosomal bovine ZFX and ZFY genes. The sequences of the ZFX and ZFY segments are reported in FIG. 2 and at SEQ ID NOS: 3 and 4 respectively. This sequence information was then used to develop PCR primers designed to produce allele-specific PCR products. One set of primers enables the specific amplification of a segment of ZFX gene, and another set enables the specific amplification of a segment of the ZFY gene. As used throughout here, the term amplification refers to making multiple duplicate copies of a DNA sequence lying between sites recognized by primers. The appearance of these allele-specific PCR amplified products allows us to determine the sex of the individual from which the DNA sample was taken.

The ZFX and ZFY genes reside in the pseudo-autosomal region of the X and Y chromosome. Therefore, males contain one copy each of the ZFX and ZFY genes while females contain two copies of the ZFX gene.

The DNA polymerase enzyme that replicates DNA in the PCR process adds nucleotides on to the 3' end of a DNA primer. The polymerase can normally initiate replication only if there is a perfect hybridization between the primer and template at the primer's 3' terminus. Therefore, we designed primers with 3' ends at locations which differed in base composition between the ZFX and ZFY genes. Optimally, other mismatches can be incorporated in the primers to increase the specificity of hybridization. As in the examples below one or more additional mismatch was incorporated near the primer 3' end to increase the severity of the existing mismatch (at the 3' terminus) between the primer and undesired template.

The assay begins with the selection of a tissue sample. Preferably, this sample is a group of cells from an embryo. As our experiments indicate, DNA from as few as two cells, and perhaps even a single cell, is sufficient for the assay. The method of isolating the embryo cells, and recovering genomic DNA from them, is not pivotal to the success of the assay. Any method of embryo and DNA isolation that results in DNA capable of PCR amplification is suitable.

The sex determination assay of the present invention then employs two rounds of DNA amplification. FIG. 1 is a flow-chart illustrating the PCR amplification steps. In the first amplification, the approximately 400 bp segment of the ZFX and ZFY genes is amplified with a primer pair that is complementary to both the ZFX and ZFY genes. This round of amplification is thus sex neutral and serves to simply amplify the number of copies of the ZFX segment and the ZFY segment, if present, for later steps. A second PCR reaction is then performed with the PCR products from the first PCR step used as templates. Primer pairs designed to hybridize to regions specific to both the ZFX gene or the ZFY gene are separately used to create X-specific and Y-specific products. Because both male and female cells contain the ZFX sequence, presence of the ZFX-specific PCR product serves as a positive control for the sex determination assay. Presence of ZFX product indicates that the reaction products all were effective and that pseudo-autosomal DNA was recovered from the embryo. Because only the male cells will contain the ZFY sequence, presence of the ZFY-specific DNA fragment indicates a male cell.

The products of the second round of PCR are examined for size, preferably by electrophoresis on an agarose gel. Presence of both the ZFY-specific and the ZFX-specific products indicates a male cell. Presence of only the ZFX-specific product indicates a female cell.

In the Examples below, the sex determination assay was performed on DNA derived from bovine lymphocytes from animals of known sex. Twelve males and twelve females were all correctly identified, verifying the accuracy of the assay. Reliability and sensitivity of the assay were examined by performing the assay on duplicate biopsies (2–8 cells) from bovine embryos. Sex determination was possible in 38 of 40 assays performed, and agreement between biopsy assays occurred in 17 of 18 cases.

2. Primer Design

Figure 2:
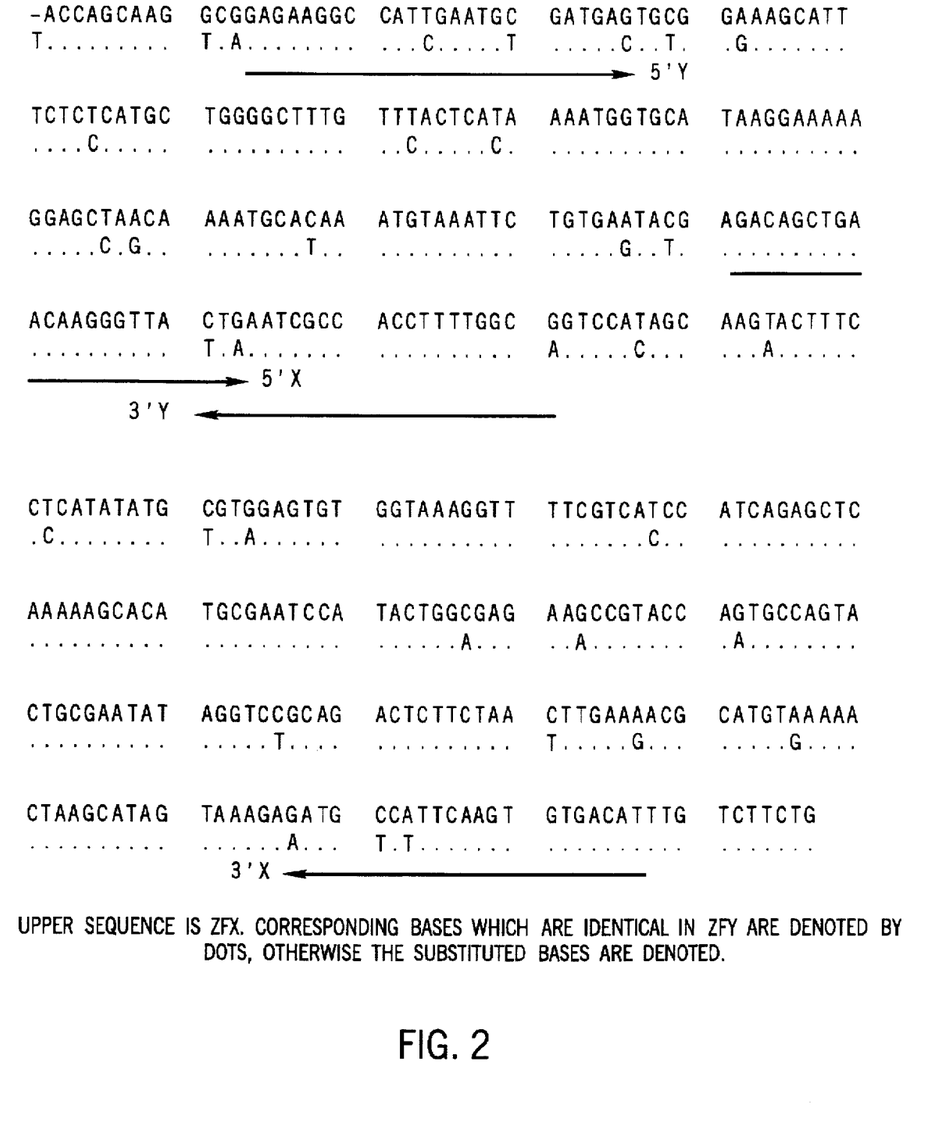
FIG. 2 is a chart illustrating the differences between the nucleotide sequence of bovine ZFX and ZFY genes and the placement of ZFX-specific and ZFY-specific primers.

The invention requires a set of X-specific and Y-specific primers. To this end, we examined the sequences of ZFX and ZFY for nucleotide differences between the two sequences. FIG. 2 illustrates these differences. Referring to FIG. 2, the sequence of ZFX is the upper sequence and ZFY is the lower sequence. Corresponding bases which are identical in ZFY are denoted by dots, otherwise the substituted bases are noted.

Taking advantage of the nucleotide changes, primers were designed to hybridize only to ZFX or ZFY sequences. For example, ZFY-specific primers should have the nucleotide found in the ZFY gene, instead of the sequence found in the ZFX gene. PCR primers used for the nested PCR reaction are preferably designed to amplify non-overlapping segments of the respective ZFX or ZFY genes. This tack is chosen to reduce the possibility of a ZFY-specific and ZFX-specific primer combining, to improperly amplify a segment of either the ZFX or ZFY gene. Using the primers described in the examples, we have observed no evidence of non-X-specific or non-Y-specific amplification.

Primer locations are preferably chosen to yield products with a size that differs enough to be readily distinguishable by simple agarose gel electrophoresis and ethidium bromide staining. The ZFY-specific product produced in the Examples below is 167 bp in length, and the ZFX-specific product is 247 bp in length. These two products are easily distinguished by size.

Since the PCR products can be directly distinguished by gel electrophoresis, there is no need for additional steps in the sex determination assay of the present invention, such as a restriction digest or radioactive hybridization, to distinguish between ZFX-specific and ZFY-specific products. Elimination of these extra steps reduces assay cost and time, the latter being critical for maximal embryo viability. This simple size assay permits the use of simple DNA specific but sequence independent non-radioactive staining, such as ethidium bromide, which is convenient and simple.

Mismatches may also be incorporated into the primer to further ensure that the X-specific primer does not hybridize to the ZFY sequence and vice versa. We have found that incorporation of up to 1–3 mismatches in a 21 nucleotide primer, depending on the location of the mismatch, still allows that primer to hybridize to its target sequence. The number and position of mismatches varies depending on primer sequence as well.

3. Bovine-specificity

Species specificity may be important to reduce assay failure due to non-bovine contamination. In addition to being rapid and sensitive, the method outlined is preferably bovine-specific. This can be achieved if one or both of the primers are designed to be bovine specific. Preferably, bovine-derived media constituents are reduced or eliminated to reduce the possibility of contaminating bovine DNA which might bias results of the sex determination assay.

One previously described sex determination assay (Aasen and Medrano, 1990, supra) faithfully amplifies the ZFX and ZFY regions from several species, not just bovine. Such broad species non-specificity is a detriment when determining embryo sex from a biopsy of few embryonic cells, since such samples are readily susceptible to accidental contamination from DNA of another species. Contaminating DNA from cells off a male technician's skin or scalp could easily be a source of contaminating Y chromosomal DNA, as could non-bovine media constituents.

Our results indicate that neither human, nor ovine, ZFY genes are effectively amplified by the ZFY-specific primers used in the Examples below. The only potential misclassification that could occur with the sex determination assay as outlined here would result from amplification of human or ovine ZFX without amplification of bovine DNA. The examples presented below with duplicate biopsies and other results (unpublished) with non-replicated biopsies indicate no departure from a 50:50 male:female sex ratio. In addition, in two cases where bovine DNA probably was absent from the PCR reaction, neither X-specific nor Y-specific bands were observed. Thus, neither human nor ovine DNA contamination has proved problematic in application of the assay when appropriate primers are chosen.

Should such contamination prove problematic, the location of the bovine ZFX-specific primers could be modified to maximize the difference between bovine and human ZFX, as well as between bovine ZFX and ZFY. This can be accomplished by aligning and comparing the bovine sequence we have generated with the published human ZFX sequence (Schneider-Gadicke et al., Cell, 57:1247–1258, 1989; Page, et al., Cell, 51:1091–1104, 1987). New bovine ZFX-specific primers could be developed with their 3' termini located in positions which differ both between the bovine ZFX and the human ZFX, and between the bovine ZFX and bovine ZFY. Comparison of the 396 bases in Table 2 across these three genes indicate that base substitutions meeting these criteria exit at 15 sites.

4. Equimolar amounts of X-specific and Y-specific products

The sex determination assay offers an improved control over alternate systems. By virtue of the nested amplification of X-specific and Y-specific bands from homologous primary PCR products, relatively equal molar amounts of X-specific and Y-specific products are obtained and visualized. A departure from relatively equal X-specific and Y-specific amplification is thus diagnostic of contaminating DNA from the media, technician or the biopsy itself (e.g., cumulus cells). An alternative sex determination assay (Herr et. al., 1990, supra) utilizes amplification of Y-specific and autosomal repetitive sequences. Equal amplification of Y-specific and autosomal segments from male DNA samples is not necessarily anticipated, and differences in amount of DNA amplified cannot be used as a diagnostic tool.

The sequence information described here could also be exploited in sex determination assays by ligase chain reaction (LCR) with or without initial PCR. LCR is a reaction in which ligase enzyme is used to ligate two adjacent oligonucleotides together, provided they complement their targets perfectly. Like PCR, LCR can be used to exponentially increase the amount of a DNA segment corresponding to a specific genomic segment. LCR can distinguish between corresponding genomic segments which differ by only a single base, and is reported to do so with extreme fidelity (F. Barany, Proc. Nat. Acad. Sci. USA, 88:189–93, 1991). An LCR assay which focused on segments differing not only between bovine ZFX and ZFY, but between bovine ZFX and human ZFX as well, would virtually eliminate any possibility of error from contaminating human DNA.

5. Sensitivity

The assay outlined here is particularly valuable due to its sensitivity. In vitro matured and fertilized ova represent an expanding source of embryos for transfer due to the reduced cost of attaining these embryos compared to embryos collected from superovulated and flushed donors. A sex determination assay which can utilize DNA from as few as 2 cells, as our assay can, will permit sex determination with minimal biopsy trauma to the embryo. This in turn may increase embryo viability.

6. Applicability To Other Mammals

The present invention is suitable for sex determination in species other than bovine. It is likely that all mammalian species contain X-specific and Y-specific sequences homologous to the ZFX and ZFY sequences. The existence of these sequences in species as diverse as mice, cattle and humans has been demonstrated. The primers described in SEQ ID NOS: 1 and 2 may be used for the first round of PCR amplification.

To prepare allele-specific primers, the amplified ZFX and ZFY fragments from the species to be analyzed should be cloned and sequenced. Sequence differences, such as those illustrated in FIG. 2, should be identified and used to construct ZFX-specific and ZFY-specific primers, as described above.

7. Use of Other Pseudo-autosomal Regions

Other pseudo-autosomal segments of the X and Y chromosome would also be suitable for use in the present invention. The regions should be characterized, as above, so that appropriate primers can be designed.

EXAMPLES

Three experiments were performed to assess the accuracy, specificity and sensitivity of our sex determination assay. The first experiment examined assay accuracy. In this experiment, DNA samples from 24 cattle of known sex (12 females and 12 males) were used as a template for the PCR reactions, and results were compared with the known sex of the cattle. In the second experiment, we examined amplification of human or ovine (from ovine serum albumin) DNA. This experiment was performed to assess the possible effects of contaminating non-bovine DNA. A third experiment examined sensitivity and accuracy of the assay when employed in sex determination of bovine embryos. For this experiment, duplicate biopsies from twenty embryos were assayed and results compared between duplicate samples.

1. DNA Cloning and Sequence Analysis

We amplified bovine ZFX and ZFY gene fragments of approximately 450 bp using PCR primers previously reported by Aasen and Medrano (supra). These PCR primers are described in Table 1 and SEQ ID NOS: 1 and 2. The amplified fragments were cloned in the pCR1000 cloning vector (Invitrogen, San Diego, Calif.) and sequenced by primer extension from both vector arms. Sequencing was performed on an automated sequencing apparatus (Applied Biosystems, Foster City, Calif.).

The DNA sequences we obtained were aligned using the GCG Sequence Analysis Software package (Devereux J., et al., Nucleic Acids Research 12,387–395 (1984)). This sequence analysis identified base substitutions at 34 out of 396 positions (FIG. 2). The sequences of the two fragments are also reported at SEQ ID NOS: 3 and 4.

2. Primer Design

We designed nested PCR primers (Table 1) to produce ZFX-specific or ZFY-specific products. As described above, we chose the primer locations to exploit the difference between the ZFX and the ZFY nucleotide sequences. As FIG. 2 indicates, the primers were positioned with the differing sequences at their 3' termini. Additional mismatches were incorporated to ensure allele-specific amplification. Specifically, these mismatches were positioned near the 3' primer terminus to enhance existing mismatches at the 3' terminus between the primer and undesired template. The exact choice and position of each added mismatch was determined empirically to permit effective amplification of the desire template and no amplification of the undesired template. In addition, primer locations were chosen to eliminate overlap between amplified regions. FIG. 1 and FIG. 2 graphically illustrate the placement of the primers relative to the ZFX and ZFY genes.

Pty. Ltd., Canberra ACT 2601 Australia) in which day 5–7 embryos were biopsied in a 10×65 mm petri dish on the stage of an inverted microscope using a finely ground surgical steel blade controlled by a micromanipulator. This method was discontinued due to the inability to precisely control cell numbers in the biopsies.

The second and more desirable method for application at the desired stage of development (day 5) involved the following steps: Embryos were held in TL Hepes media containing 10% fetal bovine serum. A small slit was made in the zona pellucida using a fine glass pipet. The desired number of embryonic cells (blastomeres) were removed by insertion of a fire-polished glass micropipet (50–60 µM outside diameter) into the slit zona and carefully aspirating

TABLE 1

| Primer | Derivation | Sequence |
| --- | --- | --- |
| 5', combined ZFX, ZFY | Aasen and Medrano (1990) | ATAATCACATGGAGAGCCACAAGCT (SEQ ID NO: 1) |
| 3', combined ZFX, ZFY | Aasen and Medrano (1990) | GCACTTCTTTGGTATCTGAGAAAGT (SEQ ID NO: 2) |
| 5' ZFX, allele-specific | this study | GACAGCTGAACAAGTGTTACTG (SEQ ID NO: 5) |
| 5' ZFY, allele-specific | this study | GAAGGCCTTCGAATGTGATAAC (SEQ ID NO: 6) |
| 3' ZFX, allele-specific | this study | AATGTCACACTTGAATCGCATC (SEQ ID NO: 7) |
| 3' ZFY, allele-specific | this study | CTGACAAAAGGTGGCGATTTCA (SEQ ID NO: 8) |

3. DNA Sample Preparation

3a. DNA Samples From Blood Or Semen

We isolated DNA samples from blood or semen from 12 bovine males and 12 bovine females as a source of DNA for verifying the accuracy of the sex determination assay. DNA for males was isolated from blood or semen. In most cases semen was used as the source of DNA for the males as a matter of convenience, because it was already available and no further animal handling was required. Source of the DNA (blood vs. semen) will not affect the results. These 24 animals were selected randomly from a genetically diverse population which contains animals of 12 different cattle breeds, Gregory et al., *Journal of Animal Science* 68,1867–76 (1990). DNA was isolated by standard methods, e.g. Strauss, *Current Protocols in Molecular Biology*, Greene Publishing and Welsey Interscience, N.Y., pp. 2.2.1–2.2.2 (1990). Approximately 25 ng of DNA was used as template in a 23 µl PCR reaction.

3b. DNA Samples From Embryos

Embryo samples were derived from in vitro matured and fertilized (IVM, IVF) embryos. Two to 10 cells were removed from compacted morulae (d 5–d 6), early-mid blastocyst (d 6–d 7) or expanding blastocysts (d 7–d 8) bovine embryos. Results (assay effectiveness) were not affected by differences in embryonic stage. Embryo biopsies were completely free of zona pellucida fragments which may contain maternal cumulus cells and/or adherent spermatozoa from the IVF procedure.

Embryos were washed 3 times in sterile media (Bavister, et al., *Biology of Reproduction*, 28,235–247 (1983)) containing 0.1–0.3% ovine serum albumin (OSA). OSA is a replacement for bovine serum albumin (BSA), the latter proving to be a source of contaminating bovine DNA which could compromise sex determination assay results. Embryo washing is required to remove bovine derived products (fetal bovine serum, BSA, and fatty acid free BSA) used in the preceding embryo culture. Each of these is a potential source of contaminating bovine DNA when using IVM-IVF derived embryos.

Two methods were used to isolate cells. The first method incorporated the use of the Twinner System (AB Technology blastomeres. Biopsied cells are washed 3 times in TL Hepes containing 0.3% OSA to remove potential bovine derived contaminants.

Embryo biopsies in 5 µl of media (TL Hepes) were immediately transferred to 0.5 ml microfuge tubes containing 20 µl of sterile water. These were held at −20° C. until the time of assay.

4. PCR Amplification Of ZFX-Specific And ZFY-Specific Segments

Primary PCR was performed with 30 tripasic cycles of denaturation at 95° C. for 60 s, annealing at 55° C. for 45 s and extension at 72° C. for 60 s as in Saiki et al., *Science* 239:487–491, 1988.

Nested PCR was performed in two stages with differing annealing temperatures. The first five PCR cycles were as previously described except for an annealing temperature of 52° C. The remaining 25 PCR cycles were performed with an annealing temperature of 60° C. Annealing temperature is raised after the initial 5 cycles to further reduce the chance of undesired template amplification (e.g., ZFX amplification by ZFY-specific primers).

With the exception of primary PCR with biopsied embryos, PCR reactions were performed in 25 µl volumes with 0.6 units of Taq Polymerase per reaction (Promega, Madison, Wis.). Reactions included 25 ng of genomic DNA as template or 1 µl of primary PCR product as template in nested PCR. 0.5 µM of each primer, 1.5 mM $MgCl_2$, 50 mM KCl, 0.001% gelatin (G2500, Sigma, St. Louis, Mo.) and 200 µM each dNTP (Boehringer Manneheim Biochemicals, Indianapolis, Ind.). Reactions were carried out in Coy Model 50 or 60 thermal cyclers (Coy Manufacturing, Ann Arbor, Mich.).

Primary PCR of embryo biopsies differed slightly. At the time of assay, biopsy tubes were removed from the freezer and placed directly in boiling water for 12–15 minutes. After boiling, the tubes were placed on the benchtop and allowed to cool to room temperature for approximately 10 minutes. Tubes were then placed on ice and 25 µl of a 2× PCR master mix was added to each. Composition of the PCR reactions are as described previously with the exception that Taq DNA polymerase concentration was 6.5-fold higher.

The discovery that higher polymerase concentrations were more effective in primary PCR from embryonic cells was made serendipitously. The reason it is more effective is unclear, but may be related to the minute amount of template DNA. Polymerase activity will decrease over ensuing PCR cycles due to the continued high temperatures. If DNA concentration is low initially (a few template copies from embryonic cells in contrast to thousands from nanogram amounts of DNA from blood cells), then PCR product yield will be low as well unless polymerase concentration is raised to provide higher than normal activity in later rounds of PCR.

5. Sample Analysis

15–20 μl of secondary PCR product was added to 3–4 μl of bromophenol blue/ficoll tracking dye (allows visual monitoring to approximate DNA migration in the gel). Samples were loaded individually in wells in a 3% (1.5% NuSieve, 1.5% SeaKem, FMC Bioproducts, Rockland, Me.) agarose gel made up in 1× Tris-borate running buffer. Samples were subject to electrophoresis for approximately 1.5 hours at 120–150 volts. Gels were stained with ethidium bromide and DNA was visualized and photographed under exposure to UV light.

6. Analysis Of DNA From Cattle of Known Sex

Figure 3A:
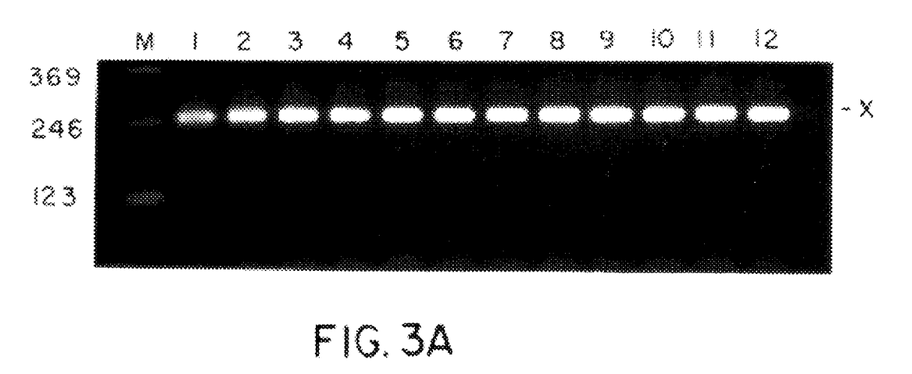
Figure 3B:
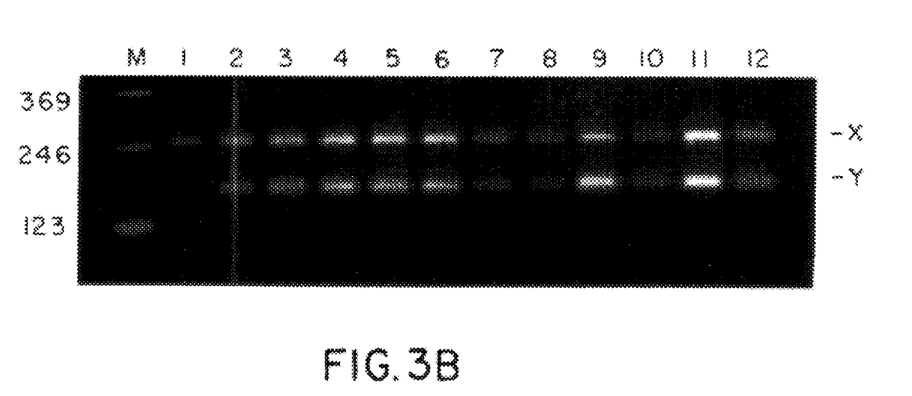

To verify the accuracy of the sex determination assay, DNA from 12 known bovine males and 12 females was used as template in PCR reactions. The sex determination assay gave correct and unambiguous results for each of these 24 individuals. FIG. 3 illustrates these results. Note that all male samples have a gel band corresponding to an X-specific and a Y-specific product and that all female samples only contain an X-specific band.

7. Analysis of DNA From Human Samples

The sex determination assay was used to analyze 8 human male and 10 human female DNA samples. We observed a ZFX-specific band for all samples. Therefore, our ZFX-specific primer is not bovine-specific. However, a ZFY-specific band was not observed for any human sample. A pair of bovine male and female DNA samples were also analyzed as a positive control. The bovine female samples yielded only the ZFX-specific band as expected. Likewise, the bovine male samples yielded both ZFX and ZFY-specific bands as expected.

OSA, used as a replacement of BSA, was also examined as a potential source of contaminating DNA for the sex determination assay. A ZFX-specific band could be amplified from OSA, but consistent amplification was achieved only at elevated concentrations (0.6%). Consequently, OSA concentrations were kept at or below 0.3% in all subsequent assays. No evidence of a ZFY-specific band was observed at any concentration of OSA.

8. Analysis of DNA From Embryos

Figure 4A:
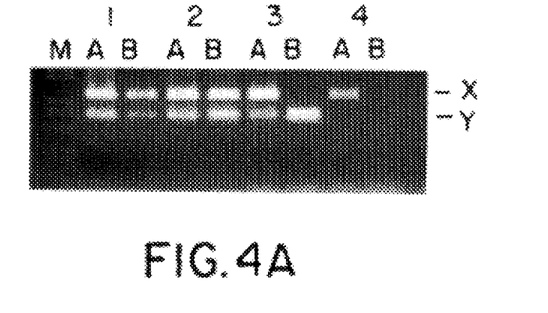
FIG. 4 is a set of stained gels containing duplicate biopsy samples taken from bovine embryos.
Figure 4B:
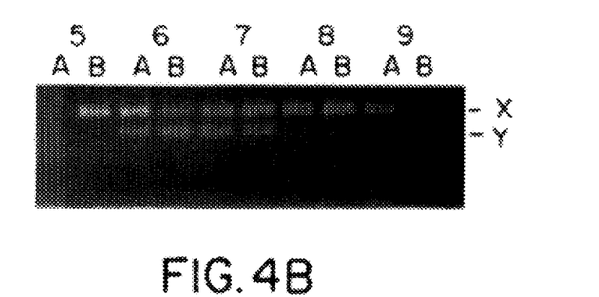
Figure 4C:
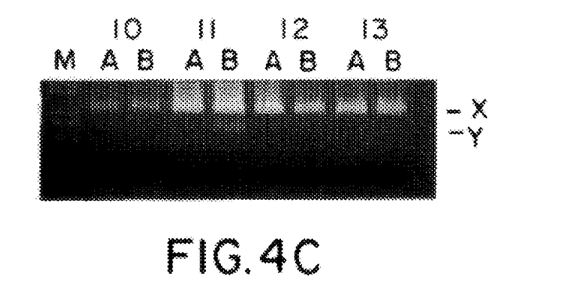

Accuracy, sensitivity and the reliability of the sex determination assay using template DNA from a limited number of cells (2–8) was examined using duplicate biopsies from in vitro matured and fertilized embryos. FIG. 4 illustrates these results. Sex determination was performed for a total of 40 biopsies (Table 2). Twenty-six of these samples are shown in FIG. 4. The designation "A" and "B" indicates the two different samples taken from an embryo.

The sex determination assay yielded a result for 38 of 40 biopsies. The two cases where no PCR product was observed (4B and 5A) are likely attributable to the loss of the sample during transfer. In both of these cases the capillary pipettes used to transfer the biopsy broke during transfer. Results of the sex determination assay were in agreement for 17 of the 18 duplicate biopsies in which both biopsies yielded a result. The basis for the disagreement between one pair of duplicate biopsies (sample 11) is unknown.

Equimolar amounts of each allele-specific product are expected and achieved on average. Sample 3B is an example of unequal product distribution.

TABLE 2

|  | Biopsy A | | Biopsy B | |
| --- | --- | --- | --- | --- |
| Embryo | Sex | Number Of Cells Assayed | Sex | Number Of Cells Assayed |
| 1 | M | 8 | M | 6 |
| 2 | M | 4 | M | 4 |
| 3 | M | 4 | M | 4 |
| 4 | F | 4 | NA | ? |
| 5 | NA | ? | F | 6 |
| 6 | M | 4 | M | 4 |
| 7 | M | 4 | M | 4 |
| 8 | F | 4 | F | 4 |
| 9 | F | 3 | F | 3 |
| 10 | F | 3 | F | 3 |
| 11 | F | 6 | M | 6 |
| 12 | F | 5 | F | 4 |
| 13 | F | 6 | F | 4 |
| 14 | M | 4 | M | 4 |
| 15 | M | 4 | M | 4 |
| 16 | M | 4 | M | 4 |
| 17 | M | 4 | M | 4 |
| 18 | M | 4 | M | 4 |
| 19 | M | 4 | M | 4 |
| 20 | M | 4 | M | 4 |

Our sex determination assay has proven successful in implanted embryos. We transferred 18 embryos that we had sexed as above into recipient cows. Twelve pregnancies resulted from these embryos. At 60 days, an ultrasound procedure determined the sex of the fetus. (Curran et al. *Animal Reproduction Science* 19:217–227, 1989; Curran et al. *Theriogeneology* 37:17–21, 1992). In 11 cases, the ultrasound sex determination matched the embryonic sex determination. The twelfth ultrasound determination was not determinative of either a male or a female fetus.

We claim:

1. A method for determining the sex of a mammalian embryo, comprising the steps of
   a) isolating DNA from at least one embryonic cell containing pseudo-autosomal DNA sequences;
   b) amplifying at least a portion of the ZFX or ZFY pseudo-autosomal DNA sequences, wherein pseudo-autosomal DNA fragments are created;
   c) amplifying both X-allele-specific and Y-allele-specific DNA sequences using the pseudo-autosomal DNA fragments as a template and using allele-specific primers, wherein each primer is 22 residues in length and contains between 1–3 mismatches relative to an allele-specific target, wherein the 3' ends of the primers are at locations which differed in base composition between the ZFX and ZFY genes wherein the mismatches are at identical locations to those in SEQ ID NOs: 5, 6, 7 and 8, wherein the X-allele-specific and Y-allele-specific amplified DNA sequences do not overlap, wherein X-allele-specific products are formed and wherein Y-allele-specific products are formed if the embryo is male; and
   d) examining the product of step (c) for the presence or absence of allele-specific products, wherein the presence of Y-allele-specific products indicates that the embryo is male and the absence of Y-allele-specific products indicates that the embryo is female.

2. The method of claim 1 wherein the amplification method of steps (b) and (c) is PCR.

3. The method of claim 1 wherein the pseudo-autosomal regions are the ZFX and ZFY regions.

4. The method of claim 1 wherein the X-allele-specific products and the Y-allele-specific products differ in number of nucleotides.

5. The method of claim 1 wherein at least one of the allele-specific primers is species-specific for the species from which the embryo is isolated.

6. The method of claim 1 wherein at least one of the allele-specific primers is bovine specific and wherein the embryo is bovine.

7. A method for determining the sex of a bovine embryo, comprising the steps of
   a) isolating DNA from at least one bovine embryonic cell containing pseudo-autosomal DNA sequences;
   b) amplifying at least a portion of the ZFX or ZFY pseudo-autosomal DNA sequences, wherein pseudo-autosomal DNA fragments are created;
   c) amplifying both X-allele-specific and Y-allele-specific DNA sequences using the pseudo-autosomal DNA fragments as a template and using allele-specific primers, wherein each primer is 22 residues in length and contains between 1–3 mismatches relative to an allele-specific target, wherein the 3' ends of the primers are at locations which differed in base composition between the ZFX and ZFY genes wherein the mismatches are at identical locations to those in SEQ ID NOs: 5, 6, 7 and 8, wherein the X-allele-specific and Y-allele-specific amplified DNA sequences do not overlap, wherein X-allele-specific products are formed and wherein Y-allele-specific products are formed if the embryo is male; and
   d) examining the product of step (c) for the presence or absence of the allele-specific products, wherein the presence of Y-allele-specific products indicates that the embryo is male and the absence of Y-allele-specific products indicates that the embryo is female.

8. The method of claim 7 wherein the amplification method of steps (b) and (c) is PCR.

9. The method of claim 7 wherein the pseudo-autosomal regions are the ZFX and ZFY regions.

10. The method of claim 7 wherein the X-allele-specific products and the Y-allele-specific products differ in number of nucleotides.

11. The method of claim 7 wherein at least one of the allele-specific primers is species-specific for the species from which the embryo is isolated.

12. A method for determining the sex of a mammalian embryo, comprising the steps of
   a) isolating DNA from at least one embryonic cell containing pseudo-autosomal DNA sequences;
   b) amplifying at least a portion of the pseudo-autosomal DNA sequences, wherein pseudo-autosomal DNA fragments are created;
   c) amplifying both X-allele-specific and Y-allele-specific DNA sequences using the pseudo-autosomal DNA fragments as a template and using allele-specific primers, wherein the primers are SEQ ID NOs: 5, 6, 7 and 8, wherein X-allele-specific products are formed and wherein Y-allele-specific products are formed if the embryo is male; and
   d) examining the product of step (c) for the presence or absence of allele-specific products, wherein the presence of Y-allele-specific products indicates that the embryo is male and the absence of Y-allele-specific products indicates that the embryo is female.

13. A method for determining the sex of a bovine embryo, comprising the steps of
   a) isolating DNA from at least one bovine embryonic cell containing pseudo-autosomal DNA sequences;
   b) amplifying at least a portion of the pseudo-autosomal DNA sequences, wherein pseudo-autosomal DNA fragments are created;
   c) amplifying both X-allele-specific and Y-allele-specific DNA sequences using the pseudo-autosomal DNA fragments as a template and using allele-specific primers, wherein the primers are SEQ ID NOs: 5, 6, 7 and 8, wherein X-allele-specific products are formed and wherein Y-allele-specific products are formed if the embryo is male; and
   d) examining the product of step (c) for the presence or absence of the allele-specific products, wherein the presence of Y-allele-specific products indicates that the embryo is male and the absence of Y-allele-specific products indicates that the embryo is female.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 25 base pairs
        ( B ) TYPE: nucleic acid ( C ) STRANDEDNESS: single
              ( D ) TOPOLOGY: linear ( i i ) MOLECULE TYPE: oligonucleotide ( x ) PUBLICATION INFORMATION:
              ( A ) AUTHORS: Aasen
                             Medrano
              ( C ) JOURNAL: Bio/Technology
              ( D ) VOLUME: 8
              ( F ) PAGES: 1279-1281
              ( G ) DATE: 1990

( x i ) SEQUENCE DESCRIPTION: SEQ ID NO:1:

ATAATCACAT GGAGAGCCAC AAGCT                                                                 25

( 2 ) INFORMATION FOR SEQ ID NO:2:

( i ) SEQUENCE CHARACTERISTICS:
              ( A ) LENGTH: 25 base pairs
              ( B ) TYPE: nucleic acid
              ( C ) STRANDEDNESS: single
              ( D ) TOPOLOGY: linear ( i i ) MOLECULE TYPE: oligonucleotide ( x ) PUBLICATION INFORMATION:
              ( A ) AUTHORS: Aasen
                             Medrano
              ( C ) JOURNAL: Bio/Technology
              ( D ) VOLUME: 8
              ( F ) PAGES: 1279-1281
              ( G ) DATE: 1990

( x i ) SEQUENCE DESCRIPTION: SEQ ID NO:2:

GCACTTCTTT GGTATCTGAG AAAGT                                                                 25

( 2 ) INFORMATION FOR SEQ ID NO:3:

( i ) SEQUENCE CHARACTERISTICS:
              ( A ) LENGTH: 396 base pairs
              ( B ) TYPE: nucleic acid
              ( C ) STRANDEDNESS: double
              ( D ) TOPOLOGY: linear ( i i ) MOLECULE TYPE: DNA (genomic)

( v i ) ORIGINAL SOURCE:
              ( A ) ORGANISM: Bovine ( x i ) SEQUENCE DESCRIPTION: SEQ ID NO:3:

ACCAGCAAGG CGGAGAAGGC CATTGAATGC GATGAGTGCG GAAAGCATTT CTCTCATGCT      60

GGGGCTTTGT TTACTCATAA AATGGTGCAT AAGGAAAAAG GAGCTAACAA AATGCACAAA     120

TGTAAATTCT GTGAATACGA GACAGCTGAA CAAGGGTTAC TGAATCGCCA CCTTTTGGCG     180

GTCCATAGCA AGTACTTTCC TCATATATGC GTGGAGTGTG GTAAAGGTTT TCGTCATCCA     240

TCAGAGCTCA AAAAGCACAT GCGAATCCAT ACTGGCGAGA AGCCGTACCA GTGCCAGTAC     300

TGCGAATATA GGTCCGCAGA CTCTTCTAAC TTGAAAACGC ATGTAAAAAC TAAGCATAGT     360

AAAGAGATGC CATTCAAGTG TGACATTTGT CTTCTG                               396

( 2 ) INFORMATION FOR SEQ ID NO:4:

( i ) SEQUENCE CHARACTERISTICS:
              ( A ) LENGTH: 397 base pairs
              ( B ) TYPE: nucleic acid
              ( C ) STRANDEDNESS: double
              ( D ) TOPOLOGY: linear ( i i ) MOLECULE TYPE: DNA (genomic)

( v i ) ORIGINAL SOURCE:
    ( A ) ORGANISM: Bovine ( x i ) SEQUENCE DESCRIPTION: SEQ ID NO:4:

| | | | | | | |
|---|---|---|---|---|---|---|
| TACCAGCAAG | TCAGAGAAGG | CCATCGAATG | TGATGACTGT | GGGAAGCATT | TCTCCCATGC | 60 |
| TGGGGCTTTG | TTCACTCACA | AAATGGTGCA | TAAGGAAAAA | GGAGCCAGCA | AAATGCATAA | 120 |
| ATGTAAATTC | TGTGAGTATG | AGACAGCTGA | ACAAGGGTTA | TTAAATCGCC | ACCTTTTGGC | 180 |
| AGTCCACAGC | AAGAACTTTC | CCCATATATG | TGTAGAGTGT | GGTAAAGGTT | TTCGTCACCC | 240 |
| ATCAGAGCTC | AAAAAGCACA | TGCGAATCCA | TACTGGAGAG | AAACCGTACC | AATGCCAGTA | 300 |
| CTGCGAATAT | AGGTCTGCAG | ACTCTTCTAA | TTTGAAGACG | CATGTGAAAA | CTAAGCATAG | 360 |
| TAAAGAAATG | TCTTTCAAGT | GTGACATTTG | TCTTCTG | | | 397 |

( 2 ) INFORMATION FOR SEQ ID NO:5:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: oligonucleotide ( x i ) SEQUENCE DESCRIPTION: SEQ ID NO:5:

GACAGCTGAA CAAGTGTTAC TG                                        22

( 2 ) INFORMATION FOR SEQ ID NO:6:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: oligonucleotide ( x i ) SEQUENCE DESCRIPTION: SEQ ID NO:6:

GAAGGCCTTC GAATGTGATA AC                                        22

( 2 ) INFORMATION FOR SEQ ID NO:7:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: oligonucleotide ( x i ) SEQUENCE DESCRIPTION: SEQ ID NO:7:

AATGTCACAC TTGAATCGCA TC                                        22

( 2 ) INFORMATION FOR SEQ ID NO:8:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: oligonucleotide ( x i ) SEQUENCE DESCRIPTION: SEQ ID NO:8:

CTGACAAAAG GTGGCGATTT CA                                        22